US00PP31672P2

(12) United States Plant Patent
Kerley et al.

(10) Patent No.: US PP31,672 P2
(45) Date of Patent: Apr. 14, 2020

(54) *PETUNIA* PLANT NAMED 'KERTEAPIC'

(50) Latin Name: *Petunia hybrida*
Varietal Denomination: KERTEAPIC

(71) Applicants: Timothy Kerley, Cambridge (GB); Sarah Kerley, Cambridge (GB); David Kerley, Cambridge (GB); Priscilla Kerley, Cambridge (GB)

(72) Inventors: Timothy Kerley, Cambridge (GB); Sarah Kerley, Cambridge (GB); David Kerley, Cambridge (GB); Priscilla Kerley, Cambridge (GB)

( * ) Notice: Subject to any disclaimer, the term of this patent is extended or adjusted under 35 U.S.C. 154(b) by 0 days.

(21) Appl. No.: 16/350,669

(22) Filed: Dec. 17, 2018

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.13
CPC ... A01H 5/02; A01H 5/00; A01H 6/82; A01H 6/824; A01H 6/1424; A01H 6/42
See application file for complete search history.

(56) References Cited

U.S. PATENT DOCUMENTS

PP30,180 P2 * 2/2019 Kleinwee ..... A01H 5/02
Plt./356.22

OTHER PUBLICATIONS

Canadian Food Inspection Agency *Petunia* Sunsurfpafure 2019, retrieved on Sep. 9, 2019, retrieved from the Internet at http://www.inspection.gc.ca/english/plaveg/pbrpov/cropreport/pet/app00006432e.shtml, 4 pp. (Year: 2019).*
RHS, retrieved on Sep. 5, 2019, retrieved from the Internet at http://apps.rhs.org.uk/agm/Award3.asp?ID=371239, one page. (Year: 2019).*
Issuu Michell's New Varieties 2018-2019, retrieved on Sep. 10, 2019, retrieved from the Internet at https://issuu.com/hfmichell/docs/newvarieties2018-2019, cover page, p. 4. (Year: 2018).*
Kerley & Co *Petunia* Tea Purple White Edge, retrieved on Sep. 10, 2019, retrieved from the Internet at https://www.kerley.co.uk/variety/purple-white-edge-2/, one page. (Year: 2019).*

* cited by examiner

*Primary Examiner* — June Hwu
(74) *Attorney, Agent, or Firm* — Cassandra Bright

(57) ABSTRACT

A new and distinct *Petunia* cultivar named 'KERTEAPIC' is disclosed, characterized by a spreading growth habit, and purple flowers with stable white rims. The plants flower freely and begin flowering under short day condition. The new variety is a *Petunia*, normally produced as an outdoor garden or container plant.

2 Drawing Sheets

Figure 1:
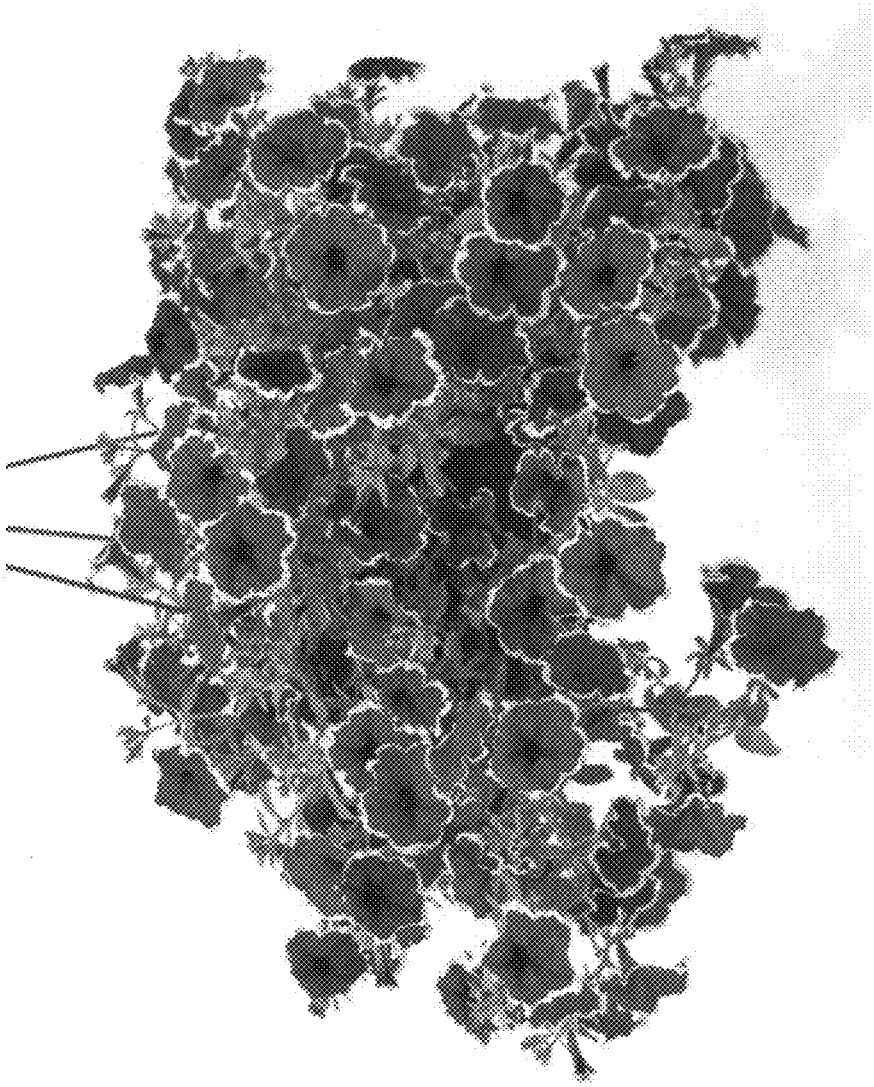

Latin name of the genus and species: *Petunia hybrida*.
Variety denomination: 'KERTEAPIC'.

BACKGROUND OF THE INVENTION

'KERTEAPIC' is a product of a breeding and selection program for ornamental *Petunia* varieties to be vegetatively propagated. The new plant of the present invention comprises a new and distinct cultivar of *Petunia* plant.

'KERTEAPIC' is a seedling resulting from the crossing of the unpatented proprietary *Petunia hybrida* referred to as '13-301-1' with the pollen parent, an unpatented, unnamed proprietary, *Petunia hybrida*, conducted in August 2013. The selection of the new variety was made in May 2014, by the inventor at a research greenhouse located in Cambridge, UK. Date of first sale was Dec. 18, 2017, in the United States. This sale was made directly by the inventor or one who obtained the claimed invention directly or indirectly from the inventor. This sale and all public disclosures made before the filing of this application fall within the exception allowed under 102(b)(1).

'KERTEAPIC' was first asexually reproduced by vegetative terminal cuttings at a research greenhouse in Cambridge, UK, September 2014. The new cultivar has been found to retain its distinctive characteristics through successive asexual propagations.

SUMMARY OF THE INVENTION

The cultivar 'KERTEAPIC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERTEAPIC' These characteristics in combination distinguish 'KERTEAPIC' as a new and distinct *Petunia* cultivar:

1. Stable white rim on purple flowers having a deep purple eye.
2. Day-length neutral flowering. Flower bud initiation occurs in day lengths of less than 8 hours.
3. Spreading plant habit.
4. Free flowering habit.
5. Medium sized *Petunia* flowers.

PARENT COMPARISON

Plants of the new cultivar 'KERTEAPIC' are similar to plants of the seed parent in most horticultural characteristics, however, plants of the new cultivar 'KERTEAPIC' differ in the following:

1. '13-301-1' has an upright plant habit, while 'KERTEAPIC' has a spreading plant habit.

Plants of the new cultivar 'KERTEAPIC' are similar to plants of the pollen parent in most horticultural characteristics however, plants of the new cultivar 'KERTEAPIC' differ in the following:

1. 'KERTEAPIC' has a stable white flower rim, the pollen parent has an unstable picotee.
2. 'KERTEAPIC' produces flowers all over the plant, the pollen parent does not produce flowers on the top of the plant.

COMMERCIAL COMPARISON

Plants of the new cultivar 'KERTEAPIC' can be compared to the commercial variety *Petunia* 'Presto Purple Picotee', unpatented. These varieties are similar in most horticultural characteristics; however, 'KERTEAPIC' differs in the following:

1. 'KERTEAPIC' has a wider and more stable white picotee.
2. 'KERTEAPIC' has a more spreading, trailing plant habit than this comparator.
3. 'KERTEAPIC' has different colored.
4. 'KERTEAPIC' has a more undulating flower margin.
5. Purple flower coloration of the new variety has a red-purple flush not found in this comparator.

Plants of the new cultivar 'KERTEAPIC' can also be compared to the commercial variety *Petunia* 'Sunsurfpafure' U.S. Plant Pat. No. 18,616. These varieties are similar in most horticultural characteristics; however, 'KERTEAPIC' differs in the following:

1. Flower production of 'KERTEAPIC' begins earlier than 'Sunsurfpafure'.
2. 'Sunsurfpafure' has an upright plant habit, which then lodges over to trailing, while 'KERTEAPIC' has a spreading plant habit throughout the production cycle.
3. 'KERTEAPIC' has a larger, more stable white flower rim than this comparator.
4. 'KERTEAPIC' has shorter branches than this comparator.

BRIEF DESCRIPTION OF THE PHOTOGRAPHS

The accompanying photograph in FIG. 1 illustrates in full color a typical plant of 'KERTEAPIC' grown in a greenhouse, in Cambridge, United Kingdom.

Figure 2:
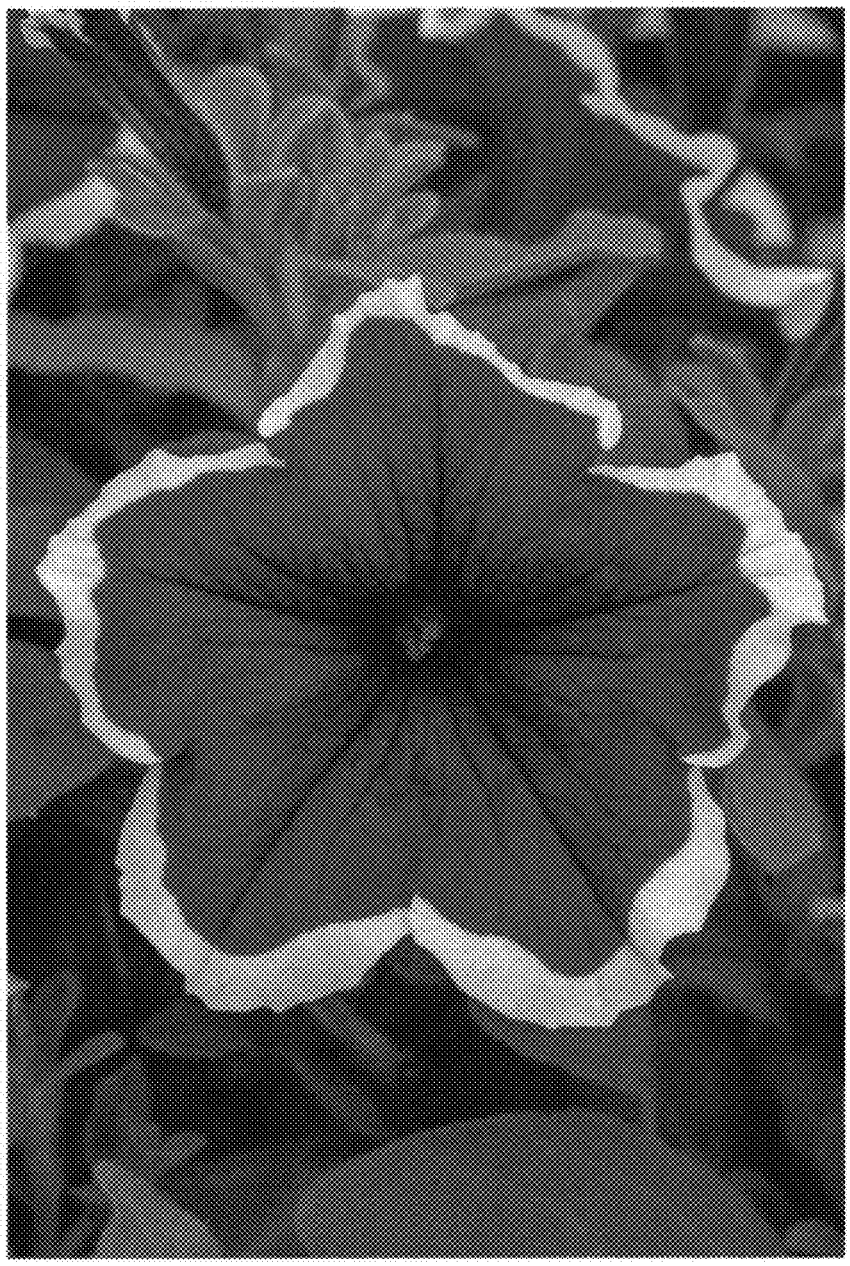

FIG. 2 illustrates in full color a typical mature flower of 'KERTEAPIC' during Spring. Age of the plant photographed is approximately 60 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KERTEAPIC' plants grown in greenhouse in Cambridge, United Kingdom, under natural lighting. Measurements were taken during April of 2018. The plants were approximately 16 weeks old from a rooted cutting in a 1.5 liter pot. The growing temperature ranged from 20° C. to 35° C. during the days, 17° C. to 23° C. during the nights. Measurements and numerical values represent averages of typical plant types.

Botanical classification: *Petunia hybrida* 'KERTEAPIC'.

PROPAGATION

Time to initiate roots: Approximately 10 days at 20° C.

Root description: Fibrous, freely branching. White, to light tan, not accurately measured with RHS chart.

Time to produce a rooted cutting: About 21 to 28 days.

PLANT

Growth habit: Spreading, mounded.

Pot size of plant described: 1.5 liter.

Height: 14.0 cm to top of flowering plane.

Plant spread: 35.0 cm.

Growth rate: Moderate.

Length of primary lateral branches: 39.3 cm.

Diameter of lateral branches: 0.5 cm.

Quantity of primary lateral branches: 5.

Characteristics of primary lateral branches:

*Color.*—Young stem: RHS Yellow-Green 144B. Mature stem: RHS Yellow-Green 146A.

*Texture.*—Densely pubescent.

*Strength.*—Medium to strong.

Internode length: 2.63 cm.

FOLIAGE

Leaf:

*Arrangement.*—Alternate before flowering, then opposite.

*Form.*—Simple.

*Quantity.*—36 per main branch.

*Average length.*—3.3 cm.

*Average width.*—1.8 cm.

*Shape of blade.*—Ovate.

*Apex.*—Acute.

*Base.*—Broad attenuate.

*Margin.*—Entire. Slightly undulating.

*Texture of top surface.*—Sparsely pubescent.

*Texture of bottom surface.*—Sparsely pubescent.

*Color.*—Young foliage upper side: Darker than RHS Yellow-Green 146A, 146B. Young foliage under side: RHS Yellow-Green 146C. Mature foliage upper side: RHS Yellow-Green 146A. Mature foliage under side: RHS Yellow-Green 146B.

*Venation.*—Type: Pinnate. Venation color upper side: Between RHS Yellow-Green 144A. Venation color under side: RHS Yellow-Green 146B.

*Petiole.*—Length: 0.5 cm. Diameter: 0.2 cm. Color: RHS Yellow-Green 144A. Texture: Densely pubescent.

FLOWER

Natural flowering season: Spring and Summer in Cambridge, United Kingdom.

Days to flowering from rooted cutting: 21 to 28 days.

Inflorescence and flower type and habit: Simple, salverform.

Rate of flower opening: Typically about 2 days from bud to fully opened flower.

Flower longevity on plant: 7 to 8 days.

Approximate quantity of flowers per plant: Average 22 flowers and 12 buds on a plant of this age.

Persistent or self-cleaning: Self-cleaning.

Bud:

*Shape.*—Oblong.
*Length.*—4.0 cm.
*Diameter at apex.*—2.1 cm.
*Diameter at base.*—0.4 cm.
*Texture.*—Densely pubescent.
*Color.*—RHS Purple N77B, venation N77A. Apex White N155A.

Flower size:

*Diameter.*—6 cm.
*Length.*—About 4.0 cm.
*Flower tube diameter at distal end.*—About 2.0 cm.
*Flower tube diameter at proximal end.*—About 0.5 cm.

Petals:

*Length from tube.*—2.9 cm.
*Length of free portion.*—1.4 cm.
*Width.*—2.8 cm.
*Quantity.*—5.
*Shape.*—Obovate.
*Appearance.*—Velvety.
*Texture, upper surface.*—Glabrous.
*Texture, lower surface.*—Densely pubescent.
*Apex.*—Acute.
*Margin.*—Entire, undulating.
*Margin coloration amount.*—Medium.
*Lobing.*—Strong.

Color:

*When opening.*—
*Upper surface.*—Darker and richer than Purple N79C, flushed Red-Purple 63A, with rim of NN155A and Green-White 157A.
*Lower surface.*—Richer than Purple N79C, slight venation of N79A. Rim of Green-White 157B.
*Fully opened.*—
*Upper surface.*—Near RHS N79C, flushed Red-Purple N66A with slight venation of N79A. Rim of 155C with 155A at apex.
*Lower surface.*—Near RHS Purple-Violet N81A with central vein of N79A. Border of 155C with 155A at apex.
*Flower throat* (*inside*).—RHS Purple-Violet N80A.
*Flower throat, vein.*—RHS Violet-Blue N92C.
*Flower tube* (*outside*).—RHS Violet 83B.
*Flower tube, vein* (*outside*).—RHS Greyed-Purple N186B.

Corolla tube:

*Length.*—3.1 cm.
*Diameter at distal end.*—2.0 cm.
*Diameter at proximal end.*—0.5 cm.
*Texture, inner surface.*—Glabrous.
*Texture, outer surface.*—Densely pubescent.

Sepals:

*Quantity per flower.*—5 fused along lower half.
*Shape.*—Cuneate.
*Length.*—1.6 cm.
*Width.*—0.4 cm.
*Margin.*—Entire.
*Apex.*—Acute.
*Texture, upper surfaces.*—Sparsely pubescent.
*Texture, upper surfaces.*—Densely pubescent.
*Color.*—Upper Surface: Between RHS Yellow-Green 146A. Lower Surface: RHS Yellow-Green 146B.

Peduncle:

*Strength.*—Moderate.
*Aspect.*—60 degrees to stem.
*Length.*—2.0 cm.
*Diameter.*—2 mm.
*Texture.*—Densely pubescent.
*Color.*—Near RHS Yellow-Green 144A.

Fragrance: None.

REPRODUCTIVE ORGANS

Stamens:

*Number.*—5 partially fused to inside of corolla tube.
*Length.*—2 cm.
*Filament length.*—1.2 cm free section.
*Filament color.*—RHS Red-Purple 72B.

Anthers:

*Length.*—3 mm.
*Shape.*—Reniform.
*Color.*—Near RHS Violet 85D.
*Pollen.*—Color: Near RHS Blue-Green 122C.

Pistil:

*Number.*—1.
*Length.*—1.8 cm.
*Style.*—Length: 1.4 cm. Color: RHS Yellow-Green 144D.
*Stigma.*—Shape: Linear. Color: RHS Yellow-Green 145A. Ovary Color: RHS Yellow-Green N144A.

OTHER CHARACTERISTICS

Seeds and fruits: Not observed to date.

Disease/pest resistance: Neither resistance nor susceptibility to the normal diseases and pests of *Petunia* have been observed. Typical well-known diseases include: *Botrytis cineria, Fusarium, Pythium, Phytophthora*, and *Rhizoctonia* species. Typical well-known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'KERTEAPIC' as herein illustrated and described.

* * * * *